United States Patent [19]

Härtel et al.

[11] Patent Number: 4,572,002
[45] Date of Patent: Feb. 25, 1986

[54] APPARATUS FOR DETERMINING THE FATIGUE LIMIT OF ELASTIC MATERIAL UNDER COMPLETELY REVERSED STRESS

[75] Inventors: Volker Härtel, Germering; Manfred Hofmann, Hünfelden, both of Fed. Rep. of Germany

[73] Assignee: Metzeler Kautschuk GmbH, Munich, Fed. Rep. of Germany

[21] Appl. No.: 585,002

[22] Filed: Mar. 1, 1984

[30] Foreign Application Priority Data

Mar. 1, 1983 [DE] Fed. Rep. of Germany ....... 3307204

[51] Int. Cl.[4] ............................................. G01N 3/32
[52] U.S. Cl. ......................................... 73/809; 73/830; 73/831; 73/834; 73/856
[58] Field of Search ................. 73/809, 830, 828, 831, 73/834, 856, 808

[56] References Cited

U.S. PATENT DOCUMENTS 4,083,233 4/1978 Seal ........................................ 73/828
4,379,410 4/1983 Fritts et al. ........................... 73/809

Primary Examiner—Anthony V. Ciarlante
Attorney, Agent, or Firm—Herbert L. Lerner; Laurence A. Greenberg

[57] ABSTRACT

In order to determine the fatigue limit of elastic materials, especially rubber, under completely reversed stress by applying a load which alternates between zero and a maximum value and in order to determine the number of load alternations which leads to the breaking of the material, a plurality of strip-shaped rubber samples are clamped between two stationary clamping beams and a rocker. The rocker is approximately parallel to the beams and is moved at one end thereof by means of a crank mechanism. The rubber samples are each positioned parallel to one another in at least one row and are alternately stretched and relaxed to a different extent, depending on their spacing from the fulcrum of the rocker.

12 Claims, 8 Drawing Figures

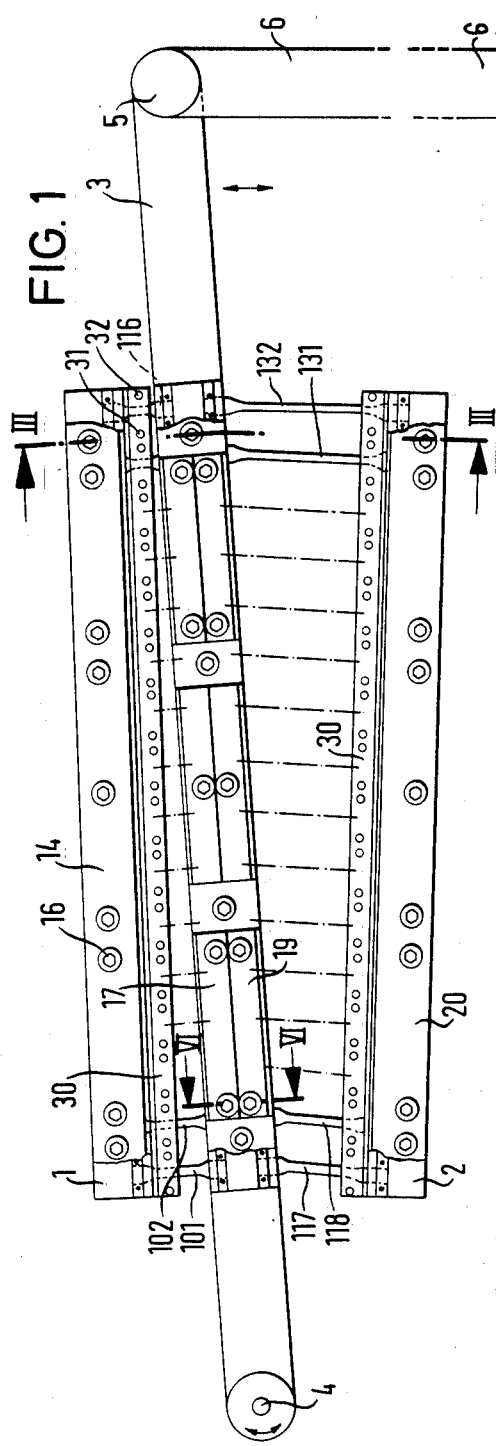
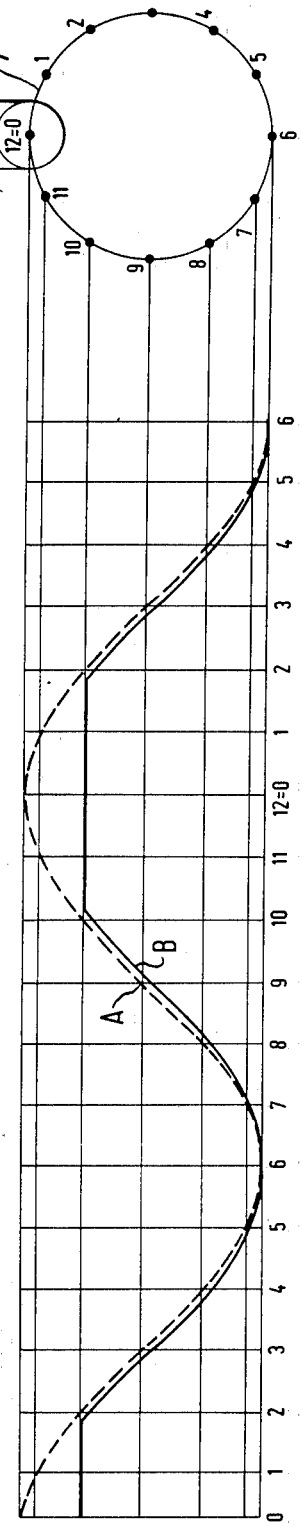
FIG. 1
FIG. 2

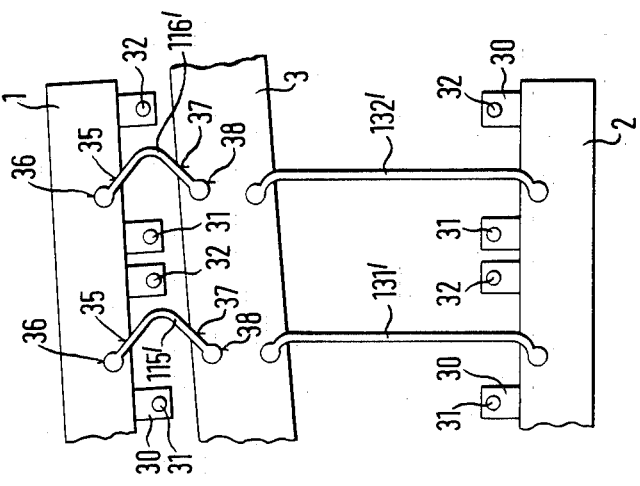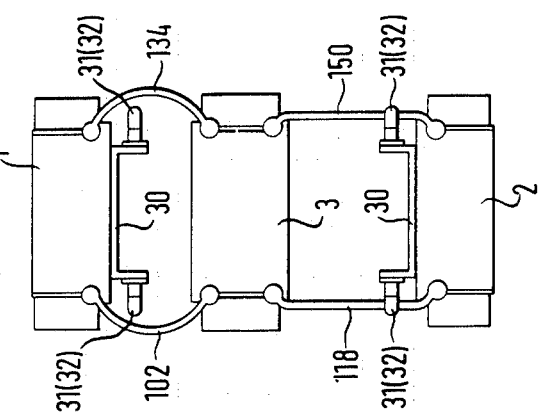

APPARATUS FOR DETERMINING THE FATIGUE LIMIT OF ELASTIC MATERIAL UNDER COMPLETELY REVERSED STRESS

BACKGROUND OF THE INVENTION

1. Field of the Invention

This invention relates to an apparatus for determining the fatigue limit of elastic materials, under completely reversed stress, in particular rubber, by applying a load which alternates between zero and a maximum value, and determining the number of load cycles which lead to the material breaking.

2. Description of the Prior Art

In order to test plastics and rubber for their dynamic loading capacity, these materials are subjected to continuous vibrations in order to determine the stresses or strains which exceed the fatigue limit under completely reversed stress and which lead to the material breaking after a certain number of alternating stresses. In this test, several identical samples are generally subjected in succession to graduated vibratory stresses and the relevent numbers of stress cycles endured are established (see "Lexikon der Kautschuk-Technik" by Jochen Schnetger, 1981, page 327). However, since it is impossible to determine an infinite fatigue limit, stresses where $10^6$ alternations of load in the vibration test are endured are usually stated as the fatigue limit under completely reversed stress in the alternating area and are represented graphically as so-called stress-cycle diagrams.

According thereto, it is known to subject individual samples of precisely prescribed dimensions to continuous vibrations of this type in suitable test machines. If, in so doing, these vibrations are applied at a frequency of 2 Hz in a device which is available on the market, then during the course of a test without a break, a period of time of about 1 week is required for the necessary endurance of $10^6$. However, since the tests have to be carried out for several strains, it is necessary to use more than one device, or a very long period of time is required, until all the desired results are obtained.

These long delays are, however, hardly beneficial and are often unjustifiable in many cases, for example during quality control or during the release of new mixtures.

BRIEF SUMMARY OF THE INVENTION

Thus, an object of the present invention is to provide an apparatus with which the fatigue limit may be determined under completely reversed stress of materials to be examined, and thus the stress-cycle diagram may be sumultaneously plotted for a broad spectrum of predetermined strains at a much faster rate than has been possible heretofore.

Accordingly, the present invention provides an apparatus for determining the fatigue limit of elastic materials under completely reversed stress, in particular rubber, by applying a load which alternates between zero and a maximum value, and determining the number of load alternations which result in the material breaking, wherein between at least one stationary clamping beam and a rocker which is positioned approximately parallel to the clamping beam and is moved outwardly at one end by means of a crank mechanism there are clamped a plurality of strip-shaped rubber samples, the samples being disposed at least in one row, being parallel to one another in each case and being alternately stretched and relaxed to a different extent depending on their spacing from the fulcrum of the rocker.

Thus, with an arrangement of this type, a large number of identical or different samples may be subjected to different strains in a single test, so that a whole series of measurements can be obtained within a much shorter time.

In order to increase the capacity, it is appropriate for one stationary clamping beam to be positioned on each side of the rocker, so that samples may be clamped on both sides of the rocker. In this arrangement, the two clamping beams may also be positioned at an angle which opens towards the crank drive side of the rocker.

Furthermore, in order to determine the number of load alternations which are endured by a rubber sample, a light barrier may be arranged in the vicinity of each sample such that the ray path is breached at least during the stretching procedure of the rubber sample which lies inbetween in each case. The light source and the photoelectric transducer of the light barrier may each be secured to the surface of the clamping beams facing the rocker and they may project into the space, spanned by the rubber samples, between the clamping beams and the rocker.

To secure the rubber samples, the samples of one test row are appropriately clamped at their thickened end regions between two clamping strips in each case, and the clamping strips are secured to the side surfaces of the clamping beams and of the rocker. Clamping strips may be positioned with rubber samples on both opposite side surfaces of the clamping beams and of the rocker, so that four rows of rubber samples are tested at the same time over all.

In this arrangement, it is appropriate if the strip-shaped samples are clamped at their end regions at an angle to the tensioning direction of the samples such that all the samples of one row arch outward when relaxed in a U-shape towards one and the same side. The clamping direction may run at an angle to the side surfaces of the clamping beams and the rocker such that the rubber samples arch outward towards these side surfaces and out of the ray path of the light barrier.

The rocker itself may be driven at a frequency of 12 Hz. Moreover, it is appropriate if the light barriers are actively connected to a counter to record the load alterations up until the respective rubber samples break. Once a complete series of tests has been concluded, it is quite straightforward to determine which samples have broken when and how many load alternations they have withstood, from which the corresponding stress-cycle diagram may then be recorded for each sample.

The construction and mode of operation of the preferred embodiment according to the present invention will now be described in detail.

BRIEF DESCRIPTION OF THE SEVERAL VIEWS OF THE DRAWINGS

FIG. 1 is a side view of the most important parts of the apparatus.

FIG. 2 shows the sinusoidal path of the tensile force acting on the rubber samples;

FIG. 6 shows a cross-section through the apparatus corresponding to the sectional line VI—VI in FIG. 1;

FIG. 7 is a side view of a section of the apparatus with a different variant for clamping the rubber samples; and FIG. 8 shows two side views of a typical rubber sample.

DETAILED DESCRIPTION

Figure 3:
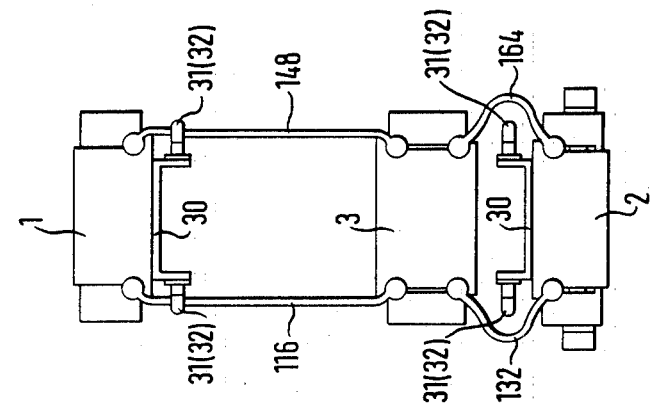
FIG. 3 shows a cross-section through the apparatus corresponding to the sectional line III—III in FIG. 1 in the highest position of the rocker.

As may be seen first of all from the side view of the apparatus shown in FIG. 1, this apparatus comprises an upper clamping beam 1 and a lower clamping beam 2 which are secured in a frame (not shown in detail) and are positioned at an angle of at most 5° from each other which opens towards the right-hand side. Between these clamping beams 1 and 2, there is positioned a rocker 3 which is mounted so that it may pivot at the left-hand end about a horizontal axis 4 and may be moved up and down in the region between the two clamping beams 1 and 2 by means of a driving rod 6 which engages the rocker 3 at the right-hand end 5 thereof and by means of a crank mechanism 7 which is diagrammatically illustrated.

A plurality of strip-shaped rubber samples 101 to 116 and 117 to 132 respectively are clamped parallel to each other between the rocker 3 and the upper clamping beam 1 on one side and between the rocker 3 and the lower clamping beam 2 on the other side. These rubber samples correspond in each case to the rubber sample which is shown in two views in FIG. 8, especially with regard to the size and shape thereof. These samples 10 have a rectangular cross-section in their middle region 11 and they merge at their ends into two cylindrical thickenings 12 and 13 which act as clamping points. Only the length P represents the actual test body, along which length the cross-section of the rubber sample 10 is constant.

FIG. 3 shows in more detail the arrangement and clamping of the rubber samples at the right-hand end of the apparatus in the region of the sectional line III—III for the position of the rocker which is shown in FIG. 1. This section also shows that the rubber samples may be positioned on both sides of the clamping beams 1 and 2 and of the rocker 3, so that according to the embodiment which is shown, a total of four rows of, in each case, 16 rubber samples, i.e. a total of 64 samples may be tested at the same time.

To this end, FIG. 3 shows that the rubber samples 101 to 116 are clamped by their upper thickening 12 between two clamping strips 14 and 15 which are attached to the upper clamping beam 1 by screws 16. The lower thickenings 13 are secured laterally to the rocker 3 in a corresponding manner between clamping strips 17 and 18. In the same way, the lower row of rubber samples 117 to 132 is fixed to the rocker 3 between suitable clamping strips 19 and 18, and to the lower clamping beam 2 between clamping strips 20 and 21. In a symmetrical manner, the right-hand rows of samples 133 to 148 and 149 to 164 are attached to the upper claping beam 2 between clamping strips 22 and 23, to the rocker 3 between clamping strips 24 and 25 and 26 respectively, and to the lower clamping beam 2 between clamping strips 27 and 28.

The individual rubber samples are clamped at their end regions approximately at an angle of 45° to the actual tensioning direction of the samples, as is shown at the lower end of the rubber sample 164, the significance of which will be explained later on.

Moreover, in the free space between the upper clamping beam 1 and the rocker 3 and between the rocker 3 and the lower clamping beam 2 light barriers are positioned in the vicinity of each rubber sample, such that the ray path of each light barrier is at least occasionally interrupted by the relevant unbroken rubber sample. As may also be seen from FIG. 3, U-shaped bows 30 are attached to the lower side of the upper clamping beam 1 and they each support a light source 31 and a photocell 32 on their free sides. These bows 30 having a light source 31 and a photocell 32 are positioned in the same way on the side of the lower clamping beam 2 facing the rocker 3. As may also be seen from FIG. 3, the rubber samples, in this case 132 and 164, will interrupt the ray path of a light barrier 31, 32 when they are stretched whereas when they are relaxed, as is shown in the case of the upper rubber samples 116 and 148, they arch laterally out of the ray path. This arching which always takes place outwards is obtained due to the fact that the samples are clamped at an angle of 45°. If during the next stretching procedure, a rubber sample should fail, the two remaining sections will always project laterally outwards because they are clamped at an angle of 45°, and they will no longer interrupt the ray path of the relevant light barrier.

The operating method of the present invention will be described below. First of all, it is assumed that all 64 measurement points are occupied by rubber samples. As a result of the upward and downward movement of the rocker 3 corresponding to the diagrammatically indicated path of the crank mechanism 7 in FIG. 2 which may be driven by an electric motor (not shown) having a speed of, for example, 720 r.p.m., corresponding to 12 Hz for the rocker 3, the rubber samples 101 to 164 are alternately stretched and relaxed. As the samples are stretched intermittently, the rocker 3 describes a path corresponding to the sine curve A shown in broken lines in FIG. 2. The force acting on a rubber sample which may be stretched to a maximum is shown by the curve B drawn in a solid line. The force path is illustrated using the rubber samples 116 and 148 at the right-hand end of the clamping beam 1. The position shown in FIGS. 1 and 3 corresponds to the point of the curve "12=0". Since in this case, the force path B is horizontal, but the rocker is at point "12=0" of the broken curve A, this means that in this position the rubber samples 116 and 148 and all the other rubber samples of the two upper rows are relaxed, as may also be seen from FIG. 3.

Figure 4:
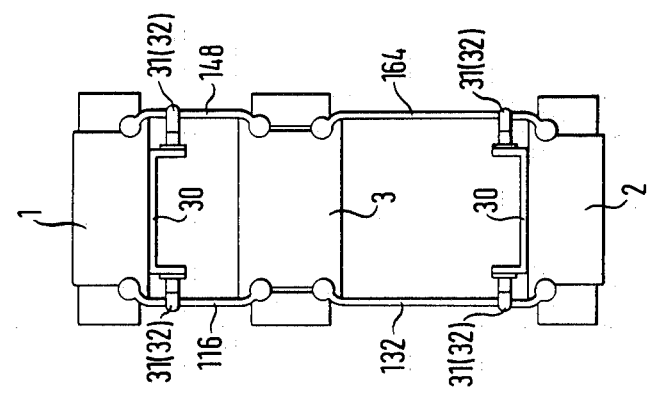
FIG. 4 shows the same cross-section in another position of the rocker.
Figure 5:
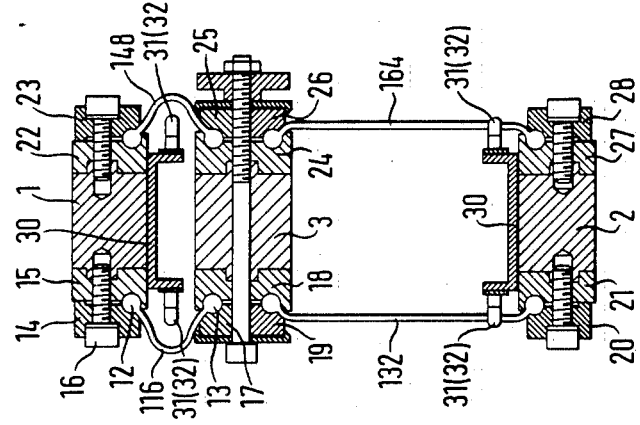
FIG. 5 shows the same cross-section in the lower position of the rocker.

When the rocker 3 moves downward again and approximately reaches the point "2" of the curve and thus reaches a position corresponding to FIG. 4, the samples 116 and 148 are stretched out straight to their normal length, without a tensile force acting thereon. A tensile force acts on the rubber samples only when the rocker moves further downwards, which tensile force reaches its maximum value in the lower position at the point "6" of the curve A and B corresponding to the position in FIG. 5, and causes an extension of 200% in the embodiment which is shown. Then, when the rocker 3 moves upwards, the extension is reduced again up to the upper relaxed position. The path for the rubber samples 117 to 132 and 149 to 164 of the two lower rows is then exactly reversed.

The conditions at the left-hand end of the apparatus in the vicinity of the fulcrum 4 of the rocker arm 3 are illustrated in FIG. 6 in the region of the rubber samples 102, 118, 134 and 150. In the upper position of the rocker 3 which is shown, the rubber samples 102 and 134 are relaxed only to a slight extent due to the short stroke of the rocker in this region, whereas the lower samples 118 and 150 are extended by a maximum of 50%.

This shows that each rubber sample is subjected to a different extension depending on its position in the apparatus or on its spacing from the fulcrum 4 of the rocker 3, which extension amounts to from 50 to 200% in the embodiment which is shown. Consequently, a large number of rubber samples having an identical or different quality may thus be subjected to different extensions and thus different strains in one test with the apparatus according to the present invention, so that the successive series of measurements which have been conventional heretofore for different strains are unnecessary and may be combined into a single series of measurements.

If the rocker 3 is driven at 12 Hz, the prescribed $10^6$ load alternations are achieved within 23 hours, so that, including the time required for removing the old samples and inserting new samples, a daily cycle for conducting one test for 64 rubber samples is possible in each case.

Reference will again be made to the function of the light barriers according to FIG. 1 and 3, in order to determine the number of load alternations which are endured by a rubber sample, or to determine the time when a rubber sample breaks. As may be seen in particular from FIG. 3, the individual rubber samples, for example 116 and 148, arch outwards to the side when they are relaxed because they are clamped at an angle of 45°, and thus they fall outside the ray path of each light barrier 31, 32. When the sample is stretched, as may be seen in the lower half of FIG. 3 in the case of the samples 132 and 164, these samples again breach the ray path of the light barrier. If one of the samples breaks, the two free ends will no longer return into the ray path because the samples are clamped at 45°, but they move out sideways, so that the ray path is no longer interrupted thereby. Since each photocell of a light barrier is connected to a corresponding counter which registers the respective interruptions in the ray path, it is possible to exactly determine when the respective sample has broken if this interruption does not occur and thus if the counter fails to respond. The stress-cycle diagram for individual samples and the corresponding different extensions may then be easily recorded therefrom at the end of each series of tests.

FIG. 3 shows a clamping arrangement of the rubber sample which causes the samples to bulge out to the side when they are relaxed and causes a brief interruption in the ray path only when the samples are stretched.

In contrast thereto, FIG. 7 illustrates another possibility of arranging the rubber samples and of the influence on the ray path of each light barrier. This figure shows a lateral view of the right-hand end of an apparatus according to FIG. 1 comprising the upper clamping beam 1, the lower clamping beam 2 and the section of the rocker 3 which lies within this region. The upper clamping beam 1 has a slit 35, which emanates from its lower side and is inclined at an angle of 45°, and a suitable circular expansion 36 at the end of the slit, which correspond to suitable slits 37 and expansions 38 in the rocker 3. Rubber samples 115' and 116' are then laterally inserted into these openings and they may be further secured with a cover strip which is not shown in detail. In the same way, the two lower rubber samples 131' and 132' are fixed between the rocker 3 and the lower clamping beam 2. In an arrangement of this type and with the rubber samples clamped in this manner, the samples will always bulge out to one and the same side when they are relaxed since they are clamped at 45°, as may be seen in the case of the two upper relaxed samples 115' and 116'.

Thus, in an arrangement of this type and with the rubber samples being clamped in this manner, each sample always lies in the ray path of a suitably positioned light barrier 31, 32. If one of the rubber samples breaks which, according to experience, happens in most cases in the vicinity of a clamping point, then in this case as well, the free ends of the samples will extend to one side, in the present case to the right-hand side, since they are clamped at 45°, so that the ray path of a light barrier 31, 32 is no longer interrupted thereby, but is unbroken. Thus, the counter connected to the respective light barrier receives a corresponding signal, from which the number of load alternations which have been endured may then also be determined.

With the apparatus according to the present invention which has been described above, it is thus easily possible to subject a large number of identical or different samples which are positioned parallel to each other to different extensions, and to determine the exact number of load alternations which have been endured by each sample. Of course, suitable modifications, in particular with respect to the number of rubber samples to be measured in parallel, and the specific arrangement thereof, as well as the use of just a single clamping beam are possible within the scope of the present invention.

We claim:

1. An apparatus for determining the fatigue limit of rubber materials under completely reversed stress, comprising two stationary clamping beams, a rocker having an end and a fulcrum, each of said stationary clamping beams being disposed on a respective side of said rocker, said rocker being substantially parallel to at least one of said clamping beams in a given position of said rocker, a crank mechanism connected to said end of said rocker for moving said rocker out of said given position, and means for clamping at least one row of mutually parallel strip-shaped samples of the rubber material between said rocker and said at least one clamping beam, the samples being alternately stretched and relaxed to a different degree depending on the distance thereof from said fulcrum of said rocker by moving said rocker to alternately apply no load and a maximum load to the samples for determining the number of load alternations resulting in breakage of the material.

2. An apparatus according to claim 1, wherein said two clamping beams are disposed at an angle relative to each other and are increasingly farther apart from each other as seen toward said end of said rocker.

3. An apparatus according to claim 1, including a light barrier having a respective part disposed on each side of the sample producing a ray path being interrupted at least during the stretching procedure of the sample.

4. An apparatus according to claim 3, wherein said light barrier parts are a light source and a photoelectric transducer secured to the surface of said clamping beams facing said rocker and projecting into a space between said clamping beams and said rocker spanned by the samples.

5. An apparatus according to claim 4, wherein said clamping means are in the form of clamping strips attached to lateral surfaces of said clamping beams and said rocker for clamping thickened end regions of the samples.

6. An apparatus according to claim 5, wherein said clamping strips clamp the samples on two opposite sides of said clamping beams and said rocker.

7. An apparatus according to claim 5, wherein the samples are clamped by said clamping strips at end regions thereof at an angle relative to the tensioning direction of the samples, such that all of the samples of one row arch outward in a U-shape to the same side when they are relaxed.

8. An apparatus according to claim 7, wherein the samples are clamped by said clamping means at an angle relative to the lateral surfaces of said clamping beams and said rocker, such that the samples arch out toward the lateral surfaces and out of the ray paths of the light barriers.

9. An apparatus according to claim 8, wherein said light barrier for each sample is operatively connected to a counter for recording the load alternations until the respective sample breaks.

10. An apparatus according to claim 3, wherein said rocker is driven at a frequency of 12 Hz.

11. An apparatus according to claim 3, wherein said light barrier for each sample is operatively connected to a counter for recording the load alternations until the respective sample breaks.

12. An apparatus for determining the fatigue limit of elastic materials under completely reversed stess, comprising two stationary clamping beams, a rocker having an end and a fulcrum, each of said stationary clamping beams being disposed on a respective side of said rocker, said rocker being substantially parallel to at least one of said clamping beams in a given position of said rocker, a crank mechanism connected to said end of said rocker for moving said rocker out of said given position, and means for clamping at least one row of mutually parallel strip-shaped samples of the elastic material between said rocker and said at least one clamping beam, the samples being alternately stretched and relaxed to a different degree depending on the distance thereof from said fulcrum of said rocker by moving said rocker to alternately apply no load and a maximum load to the samples for determining the number of load alternations resulting in breakage of the material.

* * * * *